US005744299A

United States Patent [19]

Henrickson et al.

[11] Patent Number: 5,744,299
[45] Date of Patent: Apr. 28, 1998

[54] HUMAN PARAINFLUENZA VIRUS-1 ASSAY

[75] Inventors: Kelly J. Henrickson, Oconomowoc; Jiang Fan, Wauwatosa, both of Wis.

[73] Assignee: MCW Research Foundation, Milwaukee, Wis.

[21] Appl. No.: 552,907

[22] Filed: Nov. 3, 1995

[51] Int. Cl.$^6$ .............................. C12Q 1/70; C12Q 1/68; C12P 19/34; C07H 21/04
[52] U.S. Cl. .............................. 435/5; 435/6; 435/91.2; 435/174; 536/23.1; 536/24.3; 536/24.32; 536/24.33; 536/26.6
[58] Field of Search .................... 435/5, 6, 91.2, 435/174; 536/26.6, 24.3, 24.32, 23.1

[56] References Cited

U.S. PATENT DOCUMENTS 5,200,314  4/1993  Urdea ............................................. 435/6

OTHER PUBLICATIONS

Erlich, H.A. ed. PCR Technology: Principles and Applications for DNA Amplification, Chs 1,8 and 19, 1992.
Hetherington et al. Genbank Accession No.:U01077, May 25, 1994.
Henrickson, et al., "Antibody response in children to antigen sites on human PIV-3 HN: correlation with known epitopes mapped by monoclonal antibodies," Vaccine 8:75–80 (1990).
Henrickson, et al., "Neutralizing epitopes of human parainfluenza virus type 3 are conformational and cannot be imitated by synthetic peptides," Vaccine 9:243–249 (1991).
Henrickson, K.J., "Monoclonal Antibodies to Human Parainfluenza Virus Type 1 Detect Major Antigenic Changes in Clinical Isolates," J. Infect. Dis. 164:1128–1134 (1991).
Henrickson, et al., "Genetic Variation and Evolution of Human Parainfluenza Virus Type 1 Hemagglutinin Neuraminidase: Analysis of 12 Clinical Isolates," J. Infect. Dis. 166(5):995–1005 (1992).
Henrickson, K.J., Human Parainfluenza Viruses. In, E.H. Lennette (ed.), Diagnostic Procedures for Viral, Rickettsial and Chlamydial Infections. American Public Health Association (1993).
Henrickson, et al., "Epidemiology and cost of human parainfluenza virus types 1 and 2 infection in young children," Clin. Infect. Dis. 18:770–779 (1994).
Henrickson, et al., "Recovery of human parainfluenza virus types one and two," J. Vir. Methods 46:189–206 (1994).
Henrickson, et al., "Isolation and detection methods useful for efficient recovery of human parainfluenza virus types one and two," Clin. Infect. Dis. (submitted).
Karron, et al., "Rapid detection of parainfluenza virus type 3 RNA in respiratory specimens: Use of reverse transcription–PCR–enzyme immunoassay," J. Clin. Microbiol. 32:484–488 (1994).

Primary Examiner—W. Gary Jones
Assistant Examiner—Dianne Rees
Attorney, Agent, or Firm—Quarles & Brady

[57] ABSTRACT

The present invention is a method for evaluating a biological sample for the presence or absence of human parainfluenza virus 1 (HPIV-1) infection and for the quantitation of HPIV-1. This method comprises the steps of isolating RNA from a biological sample, creating cDNA from the isolated RNA, exposing the cDNA to a pair of oligonucleotide primers selected from sequences from the group consisting of SEQ ID NOs:1–9 and inverse complements of SEQ ID NOs:1–9 under conditions in the which the primers will amplify a human parainfluenza-1 sequence if the human parainfluenza-1 virus is present, and determining whether the amplified sequence is present by EHA. The present invention is also a kit for the detection and quantitation of parainfluenza virus 1 and a kit for the detection of parainfluenza virus-1, 2 and 3 genomic RNA.

19 Claims, No Drawings

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: oligonucleotide ( x i ) SEQUENCE DESCRIPTION: SEQ ID NO:1:

ATATCAAGGA CTATAAACAT 20

( 2 ) INFORMATION FOR SEQ ID NO:2:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: oligonucleotide ( x i ) SEQUENCE DESCRIPTION: SEQ ID NO:2:

TTCTGGAGAT GTCCCGTAGG A 21

( 2 ) INFORMATION FOR SEQ ID NO:3:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: oligonucleotide ( x i ) SEQUENCE DESCRIPTION: SEQ ID NO:3:

TACCTTCATT ATCAATTGGT GATGCAATAT ATGC 34

( 2 ) INFORMATION FOR SEQ ID NO:4:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: oligonucleotide ( x i ) SEQUENCE DESCRIPTION: SEQ ID NO:4:

TATTCATCAA ACTTAATCAC TCAAGGATGT G 31

( 2 ) INFORMATION FOR SEQ ID NO:5:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: oligonucleotide ( x i ) SEQUENCE DESCRIPTION: SEQ ID NO:5:

TAAATTCAGA TATGTATCCT GAT 23

( 2 ) INFORMATION FOR SEQ ID NO:6:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: oligonucleotide ( x i ) SEQUENCE DESCRIPTION: SEQ ID NO:6:

ACCTATGACA TCAACGACAA CAGGA                                                    25

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:7:

TGGCTAAAGA AAAGACAAGT TGTCAATGTC TTAAT                                         35

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:8:

GAGACTATTC CAATAACTCA AAATTA                                                   26

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:9:

CCTATGTTGT TCAAGACAAG                                                          20

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Ile Ser Arg Thr Ile Asn
    1               5

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Phe Trp Arg Cys Pro Val Gly
    1               5

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Pro  Ser  Leu  Ser  Ile  Gly  Leu  Ala  Ile  Tyr
1                   5                        10
```

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Tyr  Ser  Ser  Asn  Leu  Ile  Thr  Gln  Gly  Cys
1                   5                        10
```

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Asn  Cys  Asp  Met  Tyr  Pro  Asp
1                   5
```

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Thr  Tyr  Asp  Ile  Asn  Asp  Asn  Arg
1                   5
```

( 2 ) INFORMATION FOR SEQ ID NO:16:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Trp  Leu  Lys  Lys  Arg  Gln  Val  Val  Asn  Val  Leu
1                   5                        10
```

( 2 ) INFORMATION FOR SEQ ID NO:17:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:17:

Glu Thr Ile Pro Ile Thr Gln Asn
1               5

( 2 ) INFORMATION FOR SEQ ID NO:18:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:18:

Pro Met Leu Phe Lys Thr
1               5

( 2 ) INFORMATION FOR SEQ ID NO:19:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:19:

ATTTCTGGAG ATGTCCCGTA GGAGAAC                                27

( 2 ) INFORMATION FOR SEQ ID NO:20:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:20:

CACATCCTTG AGTGATTAAG TTTGATGAT                              29

( 2 ) INFORMATION FOR SEQ ID NO:21:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:21:

TACCTTCATT ATCAATTGGT GATGCAATAT ATG                         33

( 2 ) INFORMATION FOR SEQ ID NO:22:

( i ) SEQUENCE CHARACTERISTICS:

(A) LENGTH: 29 base pairs
    (B) TYPE: nucleic acid
    (C) STRANDEDNESS: single
    (D) TOPOLOGY: linear ( i i ) MOLECULE TYPE: oligonucleotide ( x i ) SEQUENCE DESCRIPTION: SEQ ID NO:22:

GTCTCATGGA TTCCGATGAT TCACAGCAA  29

( 2 ) INFORMATION FOR SEQ ID NO:23:

( i ) SEQUENCE CHARACTERISTICS:
        (A) LENGTH: 28 base pairs
        (B) TYPE: nucleic acid
        (C) STRANDEDNESS: single
        (D) TOPOLOGY: linear ( i i ) MOLECULE TYPE: oligonucleotide ( x i ) SEQUENCE DESCRIPTION: SEQ ID NO:23:

GATGTACGCT GCATCATGCA GAAGCAGA  28

( 2 ) INFORMATION FOR SEQ ID NO:24:

( i ) SEQUENCE CHARACTERISTICS:
        (A) LENGTH: 33 base pairs
        (B) TYPE: nucleic acid
        (C) STRANDEDNESS: single
        (D) TOPOLOGY: linear ( i i ) MOLECULE TYPE: oligonucleotide ( x i ) SEQUENCE DESCRIPTION: SEQ ID NO:24:

AGGATATGCA TACTGGGAGC ATGTCCAACA CCA  33

( 2 ) INFORMATION FOR SEQ ID NO:25:

( i ) SEQUENCE CHARACTERISTICS:
        (A) LENGTH: 28 base pairs
        (B) TYPE: nucleic acid
        (C) STRANDEDNESS: single
        (D) TOPOLOGY: linear ( i i ) MOLECULE TYPE: oligonucleotide ( x i ) SEQUENCE DESCRIPTION: SEQ ID NO:25:

TATGGACAAT AATCCTGGTG TTATTATC  28

( 2 ) INFORMATION FOR SEQ ID NO:26:

( i ) SEQUENCE CHARACTERISTICS:
        (A) LENGTH: 28 base pairs
        (B) TYPE: nucleic acid
        (C) STRANDEDNESS: single
        (D) TOPOLOGY: linear ( i i ) MOLECULE TYPE: oligonucleotide ( x i ) SEQUENCE DESCRIPTION: SEQ ID NO:26:

TAATTTCACT AATGAATTTC CTAAGATC  28

( 2 ) INFORMATION FOR SEQ ID NO:27:

( i ) SEQUENCE CHARACTERISTICS:
        (A) LENGTH: 33 base pairs
        (B) TYPE: nucleic acid
        (C) STRANDEDNESS: single
        (D) TOPOLOGY: linear -continued (ii) MOLECULE TYPE: oligonucleotide (xi) SEQUENCE DESCRIPTION: SEQ ID NO:27:

GTGAATACAA GGCTTCTTAC AATTCAGAGT CAT    33

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:28:

ACTCTGGACT CAAGAATGAG AAAT    24

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:29:

CATATTTGAC AAATAGGCAG GCAT    24

HUMAN PARAINFLUENZA VIRUS-1 ASSAY

FIELD OF THE INVENTION

In general, the present invention relates to assays for human parainfluenza virus. In particular, the present invention relates to a PCR(amplification)-based and a direct(non-amplification)-based assay for parainfluenza virus-1.

BACKGROUND

Human parainfluenza virus type one (HPIV-1) is a major cause of lower respiratory tract infections (LRI) in infants, young children, and the immunocompromised (Henrickson, K. J., "Lower respiratory viral infections in immunocompetent children," pp. 59–96, In Aronoff SC (ed), *Advances in Pediatric Infectious Diseases*. Mosby-Year Book, Chicago, Ill., 1994; Henrickson, K. J., et al., Parainfluenza. In: Mandell, Bennet D. (ed) *Principles and Practices of Infectious Diseases. Edition 4*, Churchill Livingston, N.Y., 1994). This virus has world-wide distribution and probably contributes significantly to childhood mortality in the developing world (Henrickson, K. J., supra, 1994; Henrickson, K. J., et al., supra, 1994). In the U.S., we have demonstrated significant morbidity and cost attributable to HPIV-1 epidemics (Henrickson, K. J., et al., "Epidemiology and cost of human parainfluenza virus types one and two infections in young children," *Clin. Infect. Dis.* 18:770–9, 1994). During these epidemics, approximately 100,000 children less than five years of age are seen in emergency rooms and approximately 35,000 are hospitalized at a combined cost of approximately $90,000,000 (Henrickson, K. J., et al., supra, 1994). Currently, there is no specific therapy or vaccine for any HPIV.

We recently reported that HPIV-1 collected over a 26-year period in a single city demonstrated different genotypes and that one of these genotypes (A) had genotype-specific antigenic markers detectable using MAbs and human sera (Henrickson, K. J., "Monoclonal antibodies to human parainfluenza virus type 1 detect major antigenic changes in clinical isolates," *J. Infect. Dis.* 164:1128–34, 1991; Henrickson, K. J., et al., "Genetic variation and evolution of human parainfluenza virus type 1 hemagglutinin neuraminidase: Analysis of 12 clinical isolates," *J. Infect. Dis.* 164:1128–34, 1992). Subsequently, others have found similar antigenic changes in HPIV-1, and one report failed to find genotypes or antigenic markers over a nine-year period (Komada, H., et al., "Antigenic diversity of human parainfluenza virus type 1 isolates and their immunological relationship with Sendai virus revealed by monoclonal antibodies," *J. Gen. Virol.* 73:875–84, 1992; Hetherington, S. V., et al., "Human parainfluenza virus type 1 evolution combines cocirculation of strains and development of geographically restricted lineages," *J. Infect. Dis.* 169:248–52, 1994).

HPIV-2 outbreaks occur either biennially or yearly (B. Murphy, et al., "Seasonal pattern in childhood viral lower respiratory tract infections in Melbourne," *Med. J. Australia* 1:22–24, 1980; M. A. Downham, et al., "Diagnosis and clinical significance of parainfluenza virus infections in children," *Arch. Dis. Child* 49:8–15, 1974; P. Wright, "Parainfluenza viruses." In: R. B. Belshe ed. Textbook of Human Virology. Littleton, Mass.: PSG Publishing pp. 299–310, 1984), the majority of them appear in fall to early winter. HPIV-2 is a frequent cause of croup. It causes LRI much less frequently than HPIV-1 and HPIV-3, although the difference may be attributable to the difficulties with viral detection. Approximately 60% of HPIV-2 infections take place in the first 5 years of life; the peak incidence occurs in the second year, but significant numbers of infants are infected under 1 year of age. Although frequently overshadowed by HPIV-1 and HPIV-3, HPIV-2 can be predominant in some years (K. J. Henrickson, et al., "Epidemiology and cost of infection with human parainfluenza virus types 1 and 2 in young children," *Clin. Infect. Dis.* 18:770–779, 1994).

HPIV-3 is unique among the parainfluenza viruses in its propensity to infect young infants less than 6 months of age. LRI due to HPIV-3 causes approximately 20,000 infants and children to be hospitalized each year in the U.S. About 40% of HPIV-3 infections in the first 12 months of life lead to bronchiolitis and pneumonia. It is second only to RSV as a cause of LRI in neonates and young infants. Although endemic throughout the world, this virus also occurs in spring epidemics in North America.

Recent molecular analyses of all four serotypes has revealed more antigenic and genetic heterogeneity than had been appreciated previously (K. J. Henrickson, "Monoclonal antibodies to human parainfluenza virus type 1 detect major antigenic changes in clinical isolates," *J. Infect. Dis.* 164:1128–1134, 1991; K. J. Henrickson, et al., "Genetic variation and evolution of human parainfluenza virus type 1 hemagglutinin neuraminidase: Analysis of 12 clinical isolates," *J. Infect. Dis.* 166:995–1005, 1992; K. Prinoski, et al., "Evolution of the fusion protein gene of human parainfluenza virus 3," *Virus Res.* 22:55–69, 1992; M. Tsurudome, et al., "Extensive antigenic diversity among human parainfluenza type 2 virus isolates and immunological relationships among paramyxoviruses revealed by monoclonal antibodies," *Virology* 171:38–48, 1989; T. I. Yorlova, et al., "Studies of natural population variability of parainfluenza viruses during their epidemic circulation," *Acta Virol.* 25:64–70, 1991; K. L. van Wyke Coelingh, et al., "Antigenic variation in the hemagglutinin-neuraminidase protein of human parainfluenza type 3 virus," *Virology* 143:569–582, 1985; H. Komada, et al., "Strain variation in parainfluenza virus type 4, *J. Gen. Virol.* 71:1581–1583, 1990; H. Komada, et al., "Antigenic diversity of human parainfluenza virus type 1 isolates and their immunological relationship with Sendai virus revealed by monoclonal antibodies," *J. Gen. Virol.* 73:875–884, 1992). It appears that all four major HPIV types have virus subgroups that have unique antigenic and genetic characteristics. This includes variability even within HPIV-4 subtypes (H. Komada, et al., supra, 1990). The evolution of these viruses appears to be similar in pattern to influenza B. Most HPIV strains have type-specific antigens that will react in polyclonal serologic testing as previously described. However, HPIV-1 and HPIV-3 have subgroups (A and B) showing progressive antigenic changes (K. J. Henrickson, supra, 1991; K. Prinoski, et al., supra, 1992). Furthermore, HPIV-1 strains isolated over the past 10 years show persistent antigenic and genetic differences compared to the 1957 type strain (K. J. Henrickson, supra, 1991; K. J. Henrickson, supra, 1992; H. Komada, et al., supra, 1992). Because of this, standard reference sera prepared to HPIV isolates from the 1950s, or antigen prepared from these same "type" strains, may not react in current serologic assays.

Detection methods for human parainfluenza viruses 1, 2 and 3 currently include standard viral culture of the suspected infected fluid or tissue. This is a slow and expensive process that may take up to ten days to isolate the virus, and in the best hands, may have a sensitivity of only 40–50%. Direct antigen detection using immunofluorescence is also available both in this country and throughout the world, but the detection rate for HPIV by this method is highly variable with sensitivities averaging only in the 50–70% range and specificities being in the 80–90% range.

A published method concerning the use of an RT-PCR ELISA for the detection of a human parainfluenza virus type-3 was disclosed by Karron in the *Journal of Clinical Microbiology* (February, 1994, pp. 484–488) entitled "Rapid detection of parainfluenza virus type 3 RNA in respiratory specimens: Use of a reverse transcription-PCR-enzyme-immunoassay." The methods described in this paper are specific for an assay to detect human parainfluenza virus type 3 using specific sequences from the HN gene of HPIV-3. However, their methodology is different from the present invention because the present invention allows for the detection of HPIV-1, 2, and 3 in a single test. Furthermore, the present invention allows for the quantitation of HPIV genomic RNA in a clinical sample.

A fast and efficient method for detection and quantitation of human parainfluenza virus 1, 2 and 3 from a biological sample is needed.

SUMMARY OF THE INVENTION

The present invention is a method for evaluating a biological sample for the presence or absence of human parainfluenza virus-1 infection by use of an amplification reaction, such as the polymerase chain reaction. This method comprises the steps of isolating RNA from a biological sample and creating cDNA from the isolated RNA. The cDNA is exposed to a pair of oligonucleotide primers selected from the group consisting of SEQ ID NOs:1–9. In this embodiment of the present invention, one primer will be in the same 5'-3' orientation presented in SEQ ID NOs:1–9 and the other primer will be in the inverse complement orientation. This exposure is under conditions in which the primers will amplify a human parainfluenza virus-1 sequence if the sequence is present. The sample is then examined to determined whether an amplification product exists. The presence of an amplification product indicates that the sample was infected with human parainfluenza virus-1.

The present invention is also a method for evaluating a biological sample for the presence or absence of human parainfluenza virus-1 infection. This method comprises the steps of isolating RNA from biological sample. Then this RNA is exposed to a probe selected from the group of SEQ ID NOs:1–9 and complements of SEQ ID NOs:1–9. This exposure is under conditions that allow a hybridization reaction to occur if the probe is in the presence of a complementary nucleic acid. The sample is then examined for the presence or absence of a hybridization product. The presence of a hybridization product indicates that the sample contains human parainfluenza virus-1 nucleic acid and that the patient is infected with parainfluenza virus-1.

In a preferred embodiment of the present invention, the PCR product described above is anchored onto a solid support, such as a microtiter plate, and detected via an enzyme labeled probe. We have named this method of analyzing a PCR product "PCR-EHA" for PCR-enzyme hybridization assay.

The present invention is also a PCR-ELISA-based method of detecting human parainfluenza virus infection of a biological sample comprising the steps of isolating RNA from a biological sample, creating cDNA from the isolated RNA and exposing the cDNA to a primer pair specific for a human parainfluenza sequence under conditions permitting an amplification reaction. An amplification product will be formed if the sample contains human parainfluenza virus. The results of the amplification procedure are exposed to a protein-linked oligonucleotide probe, wherein the probe is of a sequence identical to a human parainfluenza sequence and wherein the protein-linked probe is attached to a solid support. One then determines whether the amplification product has hybridized to the oligonucleotide.

It is an object of the present invention to detect human parainfluenza virus-1 sequences.

It is another object of the present invention to detect human parainfluenza virus-1 infection.

It is another object of the present invention to detect hemagglutinin neuraminidase sequences.

It is another object of the present invention to quantitate, HPIV-1 sequences, HPIV-1 infection, HN sequences and HPIV-1, 2 and 3 sequence within a biological sample.

It is another object of the present invention to detect human parainfluenza virus-1, 2 and 3 infection.

It is another object of the present invention to provide primers and probes by which one may design a human parainfluenza virus-1 assay.

It is another object of the present invention to detect human parainfluenza infection by use of protein-linked oligonucleotides specific for a human parainfluenza sequence in a PCR-EHA assay.

It is a feature of the present invention that one may detect human parainfluenza virus-1 infection by a PCR-EHA assay.

Other objects, features and advantages of the present invention will become apparent after examination of the specification and claims.

DESCRIPTION OF THE INVENTION

In General

In one embodiment, the present invention is an assay for human parainfluenza-1 (HPIV-1). This assay comprises the steps of exposing a cDNA created from RNA isolated from a biological sample to oligonucleotide primers chosen from the group described below in Table 1. The sample may then be examined for the presence of an amplification product.

In another embodiment, these nine sequences may be used to design a probe which would be used to hybridize to nucleic acid sequences that are diagnostic for HPIV-1.

In another embodiment, the present invention is an assay for human parainfluenza virus types 1, 2, and 3. In this embodiment of the present invention, primers obtained from the sequences described below in Table 1 are combined with primers known in the art to be specific for HPIV-2 and HPIV-3. This assay would enable a clinician to determine whether a particular patient sample was positive for any of the three human parainfluenza virus types.

In another embodiment, the present invention is an assay for human parainfluenza. This assay comprises the steps of exposing a cDNA created from RNA isolated from a biological sample to oligonucleotide primers specific for human parainfluenza sequences. This exposure is under conditions capable of amplifying a human parainfluenza sequence if the sequence is present. The products of the PCR reaction are then exposed to a protein-linked oligonucleotide probe that has been attached to a solid support via the protein. One then determines whether the amplification product has bound to the solid support, preferably by use of enzymatic labels.

In another embodiment, the present invention is a kit for assaying human parainfluenza virus type 1 or, alternatively, a kit for assaying for human parainfluenza virus types 1, 2 and 3.

HPIV-1 Probes and Primers

The present invention requires the use of a probe or primer pairs that are diagnostic for HPIV-1 virus. To develop these probes or primers, one must first determine what genetic sequences are conserved between the many strains of HPIV-1 virus. If one were to use a sequence derived from only a few strains, one would risk not detecting an HPIV-1 strain that had mutated slightly from this group.

We had previously investigated genetic diversity in HPIV-1 by sequencing the hemagglutinin neuraminidase (HN) gene of 12 clinical isolates (Henrickson and Savatski, *J. Infect. Dis.* 166[5]:995–1005, 1992). HN is an important surface protein for this virus. Additionally, we were able to combine 13 HN sequences obtained from GenBank. (The GenBank location of the sequences we examined is listed in Appendix 1.) To this group, we added 15 isolates of HPIV-1 that we collected in 1991 during a single fall epidemic.

We compared these 15 new sequences to the known HPIV-1 sequences and looked for highly conserved nucleotide sequences. Our criteria was that the sequence should be greater than or equal to 20 nucleotides in length and contain no nucleotide changes.

Table 1 describes the 9 highly conserved nucleotide sequence regions that we obtained. Table 2 describes the predicted amino acid sequences derived from the conserved nucleotide sequences in Table 1. (The bases and amino acid designations correspond to the numbering system for the HN gene described in Henrickson and Savatski, *J. Infect. Dis.* 116[5]:995–1005, 1992).

TABLE 1

| HN base pair location: | Sequence: |
|---|---|
| 1. 342–361: | 5'-ATATCAAGGACTATAAACAT (SEQ ID NO: 1) |
| 2. 528–548: | 5'-TTCTGGAGATGTCCCGTAGGA (SEQ ID NO: 2) |
| 3. 640–673: | 5'-TACCTTCATTATCAATTGGTGATGCAATATATGC (SEQ ID NO: 3) |
| 4. 675–705: | 5'-TATTCATCAAACTTAATCACTCAAGGATGTG (SEQ ID NO: 4) |
| 5. 754–776: | 5'-TAAATTCAGATATGTATCCTGAT (SEQ ID NO: 5) |
| 6. 798–822: | 5'-ACCTATGACATCAACGACAACAGGA (SEQ ID NO: 6) |
| 7. 1173–1207: | 5'-TGGCTAAAGAAAAGACAAGTTGTCAATGTCTTAAT (SEQ ID NO: 7) |
| 8. 1251–1276: | 5'-GAGACTATTCCAATAACTCAAAATTA (SEQ ID NO: 8) |
| 9. 1734–1753: | 5'-CCTATGTTGTTCAAGACAAG (SEQ ID NO: 9) |

TABLE 2

| HN gene location: | Sequence: |
|---|---|
| 1. 96 aa–101 aa: | 5'-ISRTJN (SEQ ID NO: 10) |
| 2. 158 aa–164 aa: | 5'-FWRCPVG (SEQ ID NO: 11) |
| 3. 196 aa–205 aa: | 5'-PSLSIGLAIY (SEQ ID NO: 12) |
| 4. 207 aa–216 aa: | 5'-YSSNLITQGC (SEQ ID NO: 13) |
| 5. 234 aa–240 aa: | 5'-NCDMYPD (SEQ ID NO: 14) |
| 6. 248 aa–255 aa: | 5'-TYDINDNR (SEQ ID NO: 15) |
| 7. 373 aa–383 aa: | 5'-WLKKRQVVNVL (SEQ ID NO: 16) |
| 8. 399 aa–406 aa: | 5'-ETJPJTQN (SEQ ID NO: 17) |
| 9. 560 aa–565 aa: | 5'-PMLFKT (SEQ ID NO: 18) |

Therefore, to practice the present invention, one must use a probe or primer pair derived from SEQ ID NOs:1–9. The following criteria are useful in deriving such a probe or primer.

A. Probe

A probe suitable to hybridize with a HN gene sequence will be at least 20 nucleotides in length. Preferably, a probe will be 30 nucleotides in length, and most preferably a probe will be at least 35 nucleotides in length. This length may be taken from any area of the sequence. The probe should preferably have a GC content of approximately 50%. SEQ ID NO:1 is not a preferable probe because the GC composition is too low.

The probe must be selected from SEQ ID NOs:1–9.

B. Primers

To derive primers from the Table 1 sequences, one must first choose sequences that when amplified would produce a DNA segment of sufficient length. For the PCR-ELISA technique that we described below in the Examples, one would need a DNA segment of at least 100 nucleotides. If one wishes to visualize a PCR fragment on electrophoretic gel, a smaller fragment would suffice. However, for optimum PCR amplification, a fragment of 100 nucleotides is still preferred. Preferably in both cases, the fragment should exceed 150 nucleotides.

Additionally, the primer pair should be in an orientation that permits amplification. The forward primer should be in the 5'-3' orientation depicted in Table 1. The reverse primer should be in an inverse complement orientation. The primers listed below in the Example (SEQ ID NOs:19 and 20) are examples of suitably oriented primers. One primer (SEQ ID NO:19) is the 5'-3' orientation of a portion of SEQ ID NO:2 depicted above. The other primer (SEQ ID NO:20) is the inverse complement orientation of a portion of SEQ ID NO:4.

Additionally, the primer should be chosen so that the two primers are not complementary at the 3' ends. This situation would lead to a hybridization reaction between the primers before the primers hybridize to the substrate material. A complementary region of equal to or greater than 2 nucleotides will cause an unwanted primer hybridization. Preferably, there will be no complementary region at the 3' end.

Also preferred are primers that do not have internal complementary segments that allow formation of hairpins.

The primers should be at least 20 nucleotides in length. This 20 nucleotides may be chosen from within the entire length of the sequence reported. For example, a 20 nucleotide length from SEQ ID NO:8 may start with the initial GAG or may start with the fifth nucleotide C. Primers may be longer than 20 nucleotides in length if one wishes.

As described above for probe selection, a GC percentage of approximately 50% is preferred. SEQ ID NO:1 is not a preferred primer because the GC concentration is too low.

The Example below describes a preferable method of isolating nucleic acid suitable to be amplified from a nasal wash. Briefly, the 1–2 ml specimens were emptied into transport tubes containing 2 ml of minimal essential medium supplemented with bovine serum albumin, amphotericin B, penicillin G, and gentamicin. These specimens are centrifuged and the supernatants divided and refrigerated.

RNA is preferably isolated from these supernatant samples by adding a guanidinium solution described below in the Examples. Other methods known in the art of isolating RNA would also be suitable.

The following are preferred primer pairs for PCR reactions. The numbers in Table 3 and 4 refer to the SEQ ID NO. For example, "2" indicates SEQ ID NO:2.

TABLE 3

| GROUP A | GROUP B | GROUP C | GROUP D | GROUP E | GROUP F | GROUP G |
|---|---|---|---|---|---|---|
| 2 + 3 | 3 + 5 | 4 + 5 | 5 + 7 | 6 + 7 | 7 + 8 | 8 + 9 |
| 2 + 4 | 3 + 6 | 4 + 6 | 5 + 8 | 6 + 8 | 7 + 9 | |
| 2 + 5 | 3 + 7 | 4 + 7 | 5 + 9 | 6 + 9 | | |
| 2 + 6 | 3 + 8 | 4 + 8 | | | | |
| 2 + 7 | 3 + 9 | 4 + 9 | | | | |
| 2 + 8 | | | | | | |
| 2 + 9 | | | | | | |

HN-specific oligonucleotide primer pairs and probes that are preferred for PCR-EHA are listed below in Table 4.

cation product is present, thus indicating that the biological sample is infected with human parainfluenza virus.

Biological Sample

The probe or primers derived from the Table 1 conserved sequences are exposed to a biological sample that may contain HPIV-1 virus. This biological sample is preferably a nasal wash made from nasal secretions. Preferably, one would prepare the nasal wash by standard methods known to one of skill in the art. Preferably, as described in Hendriksen, *J. Viol. Methods,* 46:189–206, 1994 or Hall and Douglas, *J. Infect. Dis.,* 131:1–5, 1975.

However, other biological fluids such as nasal aspirates or pleural fluid, preferably respiratory fluids, would also be suitable. Other body fluids such as blood or spinal fluid would all be suitable for the present invention.

TABLE 4

| GROUP A | | GROUP B | | GROUP C | | GROUP D | | GROUP E | | GROUP F | |
|---|---|---|---|---|---|---|---|---|---|---|---|
| Primer | Probe | Primer | Probe | Primer | Probe | Primer | Probe | Primer | Probe | Primer | Probe |
| 2 + 4 | 3 | 3 + 5 | 4 | 4 + 6 | 5 | 5 + 7 | 6 | 6 + 8 | 7 | 7 + 9 | 8 |
| 2 + 5 | 3, 4 | 3 + 6 | 4, 5 | 4 + 7 | 5, 6 | 5 + 8 | 6, 7 | 6 + 9 | 7, 8 | | |
| 2 + 6 | 3, 4, 5 | 3 + 7 | 4, 5, 6 | 4 + 8 | 5, 6, 7 | 5 + 9 | 6, 7, 8 | | | | |
| 2 + 7 | 3, 4, 5, 6 | 3 + 8 | 4, 5, 6, 7 | 4 + 9 | 5, 6, 7, 8 | | | | | | |
| 2 + 8 | 3, 4, 5, 6, 7 | 3 + 9 | 4, 5, 6, 7, 8 | | | | | | | | |
| 2 + 9 | 3, 4, 5, 6, 7, 8 | | | | | | | | | | |

Human Parainfluenza Probes and Primers for PCR-EHA-based Assay

The present invention is also a PCR-EHA-based method of assaying a biological sample for any type human parainfluenza. This assay depends on a protein-linked oligonucleotide specific for a human parainfluenza gene sequence linked to a solid support via the protein molecule.

The method begins with exposing a biological sample to a primer pair specific for any human parainfluenza gene. We have described above how to isolate a primer pair specific for the HN gene. The human parainfluenza genome is known to comprise a variety of genes and many of these would be diagnostic for human parainfluenza. One would first obtain a nucleotide sequence of a human parainfluenza gene that is diagnostic for human parainfluenza as opposed to other infectious agents and cellular components. This could be facilitated by searching gene banks for any known sequence similar to the candidate sequence. If no matches are found, then the candidate sequence is likely to be specific to HPIV.

One would then construct a suitable primer pair from this gene sequence. Criteria listed above will be useful in constructing such a primer pair. One would then expose RNA isolated from a suitable biological sample to this primer pair under conditions suitable for PCR amplification.

Separately, one would obtain a probe, using the criteria described above, specific for a human parainfluenza gene sequence. This probe should be attached to a protein molecule capable of binding a solid support. We have described above a procedure wherein BSA is attached to an oligonucleotide and used to bind a solid support. However, other protein molecules may be equally suitable. To determine whether a protein molecule is as suitable for the present invention as BSA, one would run a reaction with a candidate protein in parallel to a reaction with BSA and determine whether the candidate protein linked oligonucleotides attached to the plate with the same efficiency as the BSA-linked oligonucleotides.

The protein-linked oligonucleotide is then attached to a solid support in preparation for a PCR-EHA assay as described above. One then determines whether the amplifi- The present invention is especially useful for the diagnosis of HPIV-1 in immunocompromised children or adults. These patients might preferably be diagnosed by broncho alveolar lavage.

Reverse Transcription Reaction

Once RNA is isolated from the biological sample, one needs to perform a reverse transcription reaction to create a DNA template for the probes or primers.

A suitable reverse transcription reaction requires that the RNA sample be exposed to reverse transcriptase enzyme and deoxyribonucleotides so that a cDNA molecule may be created that corresponds to the initial RNA molecule.

Preferably, a reverse transcription reaction is performed as described below in the Examples.

HPIV-1 Assay

To perform the method of the present invention, one must first select a probe or primer pair as described above and expose the cDNA described above to this probe or primer pair.

A. PCR Reaction

Preferably, one would choose to use a pair of primers and examine the final product for the presence of a PCR amplification product. This examination could involve examining the products of the reaction on an electrophoretic gel and determining whether an amplified product of the appropriate size had been created. One of skill in the art of molecular biology will be aware of many protocols designed to optimize PCR reactions. Particularly useful protocols are described in *PCR Protocols,* Ed. M. Innis, et al. Academic Press, San Diego.

Most preferably, the PCR reaction will be coupled to an EHA procedure. As described below, one would anchor the PCR amplification product to a solid support and examine the support for the presence of the PCR product. This procedure could be done in several ways. We will describe two of the most preferable ways below.

PCR-EHA Method A. In this method, one first attaches the amplified product to a solid support, such as a microtiter dish. For example, a streptavidin-coated plate may be provided. One of the selected primers may be attached to a biotin molecule so that an amplification product will be labelled with biotin and bind to the streptavidin plate.

The plate and product are then exposed to an HN-specific oligonucleotide probe containing a segment of the HN sequence. This probe is attached to a marker enzyme, such as horse radish peroxidase (HRP), which may be detected via its enzymatic properties.

This protocol is described in detail in the Examples below.

PCR-EHA Method B. In PCR-EHA method B, one would attach a protein molecule capable of binding to the solid support, such as BSA, to an HN-specific oligonucleotide probe. The plate is coated with these protein-attached oligonucleotides that are available to hybridize with an amplified product. This amplified product is preferably attached to a label molecule, such as biotin, that is capable of being detected. In one embodiment, the biotin-labelled PCR product may be complexed to a streptavidin-horse radish peroxidase conjugate. One may then detect this complex with the appropriate substrate. A preferred method of performing this method is described below:

One must first derivitize the 5' phophorylated oligonucleotide probe (oligolink derivitization reagent, PIERCE). Preferably, one would place 20 ug/ul of 5'-phosphorylated oligonucleotide in a clean 1.5 ul microcentrifuge tube. Remove 200 ul of the derivitization reagent and transfer to a vial containing EDC (ethyl-3[3-dimethyl-aminopropyl] carbodiimide).

Centrifuge the tube 3 seconds in a microcentrifuge to collect reactants in the bottom of the tube. Incubate the tube at 50° C. for 30 minutes with constant mixing.

Resuspend the OligoLink™ matrix by vortexing until no solid is visible in the bottom of the tube. To an assembled spin column add 160 ul of matrix. Place the column in a microcentrifuge tube and centrifuge briefly (5 seconds) to remove the excess water. After spinning, carefully push the bottom cap onto the column. Discard the water from the collection tube.

Following the incubation period, add 81 ul OligoLink™ binding buffer to the tube containing the derivitization oligonucleotide. Mix well and transfer the entire contents to the spin column containing the OligoLink™ matrix. Screw the top cap onto the spin column and invert the column to mix the reactants. Agitate the tightly capped spin column at room temperature for 15 minutes. Following the 15 minute incubation period, spin the column for 2 seconds with caps in place to collect the reactants in the bottom of the column. Carefully remove top and bottom caps. Place the spin column in a collection tube and centrifuge for 10 seconds.

To the spin column add 500 ul OligoLink™ binding buffer. Spin for 10 seconds. Wash the OligoLink™ matrix by adding 500 ul ethanol wash buffer. Spin 10 seconds. To spin the column and another 500 ul of ethanol wash buffer, followed by 1.0 ul of DTT solution. Replace the top cap on the spin column and invert several times to suspend the matrix in the reductant. Incubate 10 minutes with occasional mixing.

Following the reduction step, spin column 2 seconds with caps in place to collect reactants in the bottom of the column then remove top and bottom caps. Place spin column in a collection tube and spin for 10 seconds. Wash the excess DTT from the column by adding 500 ul ethanol wash buffer. Spin 10 seconds.

Repeat the ethanol wash 3 more times using 500 ul of ethanol wash buffer each time. Add 160 ul H$_2$O (preheated to 55° C.), and incubate the entire column at 55° C. for 5 minutes. Remove caps and place the column in a clean 1.5 ml collection tube. Spin the column for 20 seconds. Discard eluate.

One should then prepare a maleimide activated BSA/ oligonucleotide probe complex (Imject Maleimide Activated Bovine Serum Albumin™, Pierce). Add 4 ml H$_2$O to 2 mg activated BSA. Immediately mix the oligo and 0.2 ml BSA, incubate at room temperature for 2 hours and hold at −20° C.

To coat the ELISA plate, one may follow the following procedure. Preferably Costar, EIA/RIA plates, Medium Bind-in 3591, are obtained. Make up a solution containg 30 ul oligo-BSA complex in 15 ml coating buffer. (Coating buffer is 0.2M Carbonate-Bicarbonate buffer, pH 9.4). Add 100 ul/well of this solution and incubate at 4° C. overnight. The next morning, empty plate and wash with PBS 3 times.

To block the ELISA plate, one would preferably use the following procedure: Add 300 ul/well blocking solution. (Blocking solution is 5×Denhardt's solution, 1% gelatin [EIA grade, BIORAD], 250 ug/ml herring sperm DNA.) Incubate overnight at 4° C. Remove blocking solution by aspiration next morning.

One then performs an enzyme hybridization assay. Preferably, add 70 ul/well of premixed solution for solution hybridization. Mix 5 ul denatured PCR product (denature at 95° C., 5 minutes, keep on ice, 10 minutes) and 65 ul hybridization buffer. Incubate at 42° C. 1 hour.

A preferable hybridization buffer is:

5×saline sodium phosphate EDTA

5×Denhardt's solution 1 pmol HRP-labeled HPIV-1 OR HPIV-2, or HPIV-3 HA specific probe Wash 2 times with 2×SSC at 37° C. and 8 times with PBS containing 0.05% Tween-20.

To analyze the reaction products, one would typically dilute strepavidin-HRP-conjugate 1:1000 with PBS containing 0.05% Tween-20. Add 200 ul/well and incubate at room temperature for 30 minutes. Wash 5 times with PBS containing 0.5% Tween-20. Add 200 ul/well TMB-EHA substrate buffer in the dark. Incubate at room temperature for 15 minutes with gentle agitation. Stop with 50 ul/well 1.0N H$_2$SO$_4$. Incubate with gentle agitation for 5 minutes.

To interpret results, one may read optical density (OD) at 450 nM in 30 minutes. Samples with an O.D. greater than or equal to the mean of the negative control plus 3σ of the negative control are considered positive. If the O.D. is less than this, the sample is considered negative.

To quantitate the copy number of HPIV-1 RNA in the sample, plot the EHA O.D. of the standard curve and fit each sample O.D. to this plot.

Quantification Standard

The following method is useful in constructing a quantification standard: HPIV-1 virus RNA is synthesized from HPIV-1 virus genomic RNA by reverse transcription. The cDNA is amplified with a primer pair of HN1B (ACT CTG GAC TCA AGA ATG AGA AAT, SEQ ID NO:28) and HN2A (CAT ATT TGA CAA ATA GGC AGG CAT, SEQ ID NO:29) to yield a 2070 bp HN gene product. The PCR product and plasmid PCR™II (Invitrogen, San Diego, Calif.) are ligated according to the supplier's protocol. A clone is obtained and named PCR™II 2-1. This clone contains the 2070 bp HPIV-1 HN gene insert. The clone is, preferably, confirmed first by BamHI, XbaI, BamHI/XbaI digestion and then by sequencing with USB sequences PCR product sequencing kit (United States Biochemical, Cleveland). PCR™II2-1 DNA is transcribed to RNA with SP6 RNA polymerase (Promega, Madison, Wis.). The RNA is examined on denatural agarose gel, quantitated on a spectrophotometer to obtain copy number and frozen at 70° C. A known copy number of the transcript is introduced into virus genomic RNA lysis buffer and isolated with the same procedure as virus genomic RNA isolation when it is used as a quantitative standard.

Positive and negative controls which included transcript RNA from plasmid PCR™II2-1 and PCR™II are added at each assay. The cutoff value is calculated from the mean absorbance obtained from a group of seronegative samples plus three standard deviations. Copy number from subject samples are determined from the absorbances obtained from a dilution series of an RNA HN gene construct of know copy number described previously.

B. Probe Hybridization Reaction

If one chooses to use a probe hybridization reaction as an HPIV-1 assay, one must expose the probe and viral genomic RNA under conditions known in the art to allow hybridization between the probe and HPIV-1 sequence. Preferable conditions are those described in the Examples for hybridization in the EHA reaction.

The sample is then examined for the presence of the hybridization product. Preferably, this examination would comprise labeling the probe and determining whether a double-stranded labelled product is present at the end of the assay procedure.

HPIV-1, 2 and 3 Assay

If one wishes to assay for HPIV-1, 2 and 3, one could use the method of the present invention in combination with known sequences used as primers for HPIV-2 and 3. Table 5 below describes known HPIV-2 and 3 sequences. We have demonstrated that primers and probes from these known sequences are capable of amplifying and detecting HPIV-2 and 3 by RT-CR-EHA.

HPIV-1 Assay Kit

A kit to detect HPIV-1 would contain either a selected probe or selected PCR primers labelled as described below. Additionally, substrate materials could be included, such as TMB if horse radish peroxidase is the enzyme label. A HN-specific oligonucleotide, preferably labelled, should be included.

HPIV-1 2, and 3 RT-PCR-EHA Kit

The present invention is also a kit for the detection of HPIV-1 or, alternatively, for the detection of HPIV-1, 2 and 3. The kits are different depending on which of the three preferred PCR methods for detecting HPIV sequences one wishes to use:

PCR-EHA Method A

The kit for HPIV-1, 2 and 3 would comprise three pairs of primers for HPIV-1, HPIV-2 and HPIV-3 and three different probes specific for HPIV-1, HPIV-2 and HPIV-3. Preferable probes and primers are described in Table 5. The probes would all be enzymatically labelled. Preferable enzyme labels are also described in Table 5. Preferably, the kit would also contain substrates for enzyme detection such as TMB (3',3',5',5' tetramethylbenzidine), bromoresol purple, and PNPP (p-nitrophenylphosphate).

The procedure for using this kit would be as follows:
1. The three pairs of primers for HPIV-1, HPIV-2, and HPIV-3 are added in each of 3 tubes. A PCR reaction is then performed and PCR products are obtained.
2. The HPIV-1 probe, HPIV-2 probe and HPIV-3 probe are labeled with HPRO, AP and urease, respectively.
3. One would then perform the EHA procedure described below in the Examples. One would preferably add 200 µl/well TMB-EHA substrate for HPIV-1 detection in one well, PNPP for HPIV-3 detection in another well and bromoresol purple for HPIV-2 detection in the third well.

PCR-EHA Method B

A different kit is necessary if one wishes to use PCR-EHA method B. In this kit, one would provide three pairs of primers for HPIV-1, 2 and 3 and three HN-specific oligonucleotide probes for HPIV-1, 2 and 3. The oligonucleotides would all be attached to a protein molecule suitable for binding a solid support, such as BSA. One primer from each primer pair should be enzymatically labelled. The general procedure of PCR-EHA Method B is as follows:
1. Three pairs of primers for HPIV-1, HPIV-2, and HPIV-3 are added in each PCR tube. A PCR reaction amplifies any HPIV-1, 2 or 3 sequences.
2. BSA/HPIV-1 oligonucleotide complex, BSA/HPIV-2 oligonucleotide complex, and BSA/HPIV-3 oligonucleotide complex are coated on microtiter plates separately.
3. The products of step 1 are combined with the labelled probes and hybridization products are detected. The PCR-EHA procedure B is described above.

Alternatively, one may wish to use PCR-EHA method B with probes that are not specific for the HN protein. A suitable kit for this method would provide at least one pair of primers specific for human parainfluenza virus genome and one protein-linked oligonucleotide probe specific for the human parainfluenza virus amplification product. As above, one primer from the primer pair should be enzymatically labelled. The general procedure of PCR-EHA method B, as described above, would then be followed. Preferably, one would provide three pairs of primers and three probes specific for sequences found in human parainfluenza-1, 2 and 3 in the kit.

PCR Method C

The third PCR method is simply a PCR reaction and visualization of the PCR product. For the third PCR method, one would simply need to provide three pairs of primers for HPIV-1, 2 and 3. After the amplification reaction the PCR products would be examined on a electrophoretic gel, preferably a 2% agarose gel, and visualized. This visualization is preferably via ethidium bromide staining.

If the primers and probes described in Table 5 are used, the PCR product size for HPIV-1 is 180, for HPIV-2 is 244, and for HPIV-3 is 278 bp, respectively. The density of the band is examined by densitometry and compared with a standard.

We have successfully used the kit described above to assay biological samples for human parainfluenza virus-1, 2 and 3.

TABLE 5

PRIMERS AND PROBES USED IN HPIV-1, HPIV-2, HPIV-3 PCR-EHA KIT

| SUBTYPE | SEQUENCE | SIZE/PCR PRODUCT | ENZYME LABLING | SUBSTRATE |
|---|---|---|---|---|
| HPIV-1 | 5' Primer: ATT, TCT, GGA, GAT, GTC, CCG, TAG, GAG, AAC (SEQ ID NO: 19) 3' Primer: Biotin-CAC, ATC, CTT, GAG, TGA, TTA, AGT, TTG, ATG, A (SEQ ID NO: 20) | 180 | | |
| | Probe: TAC, CTT, CAT, TAT, CAA, TTG, GTG, ATG, CAA, TAT, ATG (SEQ ID NO: 21) | | HRPO | TMB |
| HPIV-2 | 5' Primer: GTC, TCA, TGG, ATT, CCG, | 244 | | |

TABLE 5-continued

PRIMERS AND PROBES USED IN HPIV-1, HPIV-2, HPIV-3 PCR-EHA KIT

| SUBTYPE | SEQUENCE | SIZE/PCR PRODUCT | ENZYME LABLING | SUBSTRATE |
|---|---|---|---|---|
| | ATG, ATT, CAC, AGC, AA (SEQ ID NO: 22) | | | |
| | 3' Primer: GAT, GTA, CGC, TGC, ATC, ATG, CAG, AAG, CAG, A (SEQ ID NO: 23) | | | |
| | Probe: AGG, ATA, TGC, ATA, CTG, GGA, GCA, TGT, CCA, ACA, CCA (SEQ ID NO: 24) | | Urease | Bromoresal Purple |
| HPIV-3 | 5' Primer: TAT, GGA, CAA, TAA, TCC, TGG, TGT, TAT, TAT, C (SEQ ID NO: 25) | 278 | | |
| | 3' Primer: TAA, TTT, CAC, TAA, TGA, ATT, TCC, TAA, GAT, C (SEQ ID NO: 26) | | | |
| | Probe: GTG, AAT, ACA, AGG, CTT, CTT, ACA, ATT, CAG, AGT, CAT (SEQ ID NO: 27) | | AP | PNPP |

Example 1. Detection and Quantification of HPIV-1 HN Gene Amplification Products by a Nonisotopic System: RT-PCR-EHA.

The following describes our procedure for assaying nasal wash samples for HPIV-1:

1. Collection of nasal wash specimens.

Standard nasal washes were carried out on patients suspected of having a parainfluenza virus infection.

The specimens averaged 1–2 ml and were immediately emptied into transport tubes containing 2 ml of minimum essential medium (MEM) supplemented with 0.5% bovine serum albumin, gentamicin (5 μg/ml).

Transport tubes were kept at room temperature 0.5–3 hours in the emergency room before being refrigerated at 4° C.

The specimens were centrifuged at 2000×g for 15 minutes, and the supernatants were then divided. 0.5–1 ml aliquots were refrigerated at 4° C., until frozen at −80° C. later that day.

2. Construction of the quantitation standard.

The quantitation standard was a 2070-base RNA transcript of a plasmid designated PCR™II2-1. To construct this standard, HPIV-1 virus RNA was synthesized from HPIV-1 virus genomic RNA by reverse transcription. The cDNA was amplified with a primer pair of HN1B (ACT CTG GAC TCA AGA ATG AGA AAT, SEQ ID NO:28) and HN2A (CAT ATT TGA CAA ATA GGC AGG CAT, SEQ ID NO:29) to yield a 2070 bp HN gene product.

The PCR product and plasmid PCR™II (InVitrogen, San Diego, Calif.) were ligated under standard conditions. Transformation of INVaF'-competent cells (InVitrogen, San Diego, Calif.) with the ligated plasmid was carried out according to the suppliers protocol. A clone was obtained and named PCR™II2-1. This clone contained the 2070 bp HPIV-1 HA gene insert.

The clone was checked first by Bam HI, Xba I, Bam HI/Xba I digestion and then by sequencing with USB sequenase PCR product sequencing kit (United States Biochemical, Cleveland).

PCR™II2-1 DNA was transcribed to RNA with SPG RNA polymerase (Promega, Madison, Wis.). The RNA was viewed on a denatured agarose gel, quantitated on a spectrophotometer to obtain correct copy number, and frozen at −70° C.

3. RNA Isolation

Into a sterile 1.5 ml microfuge tube, 0.5 ml guanidinium solution was added to 100–200 ul tissue culture supernatant or the clinical nasal wash described above. The guanidinium solution was:

| Guanidinium (iso)thiocyanate | 4M |
|---|---|
| Sodium Citrate, pH 7 | 25 mM |
| Sarcosyl | 2% (w/v) |
| 2-mercaptoethanol | 0.1M |

The samples were homogenized by vortexing. 50 μl (1/10 volume) of 2M sodium acetate pH 4 was added. 500 μl (1 volume) water saturated phenol (pre-warmed) was added. 100 μl (1/5 volume) chloroform isoamyl alcohol (49:1) was added.

The mixed solution was vortexed thoroughly and then cooled on ice 5 minutes. The suspension was centrifuged in a microfuge at full speed for 15 minutes at 4° C. The RNA was present in the top aqueous phase whereas DNA and proteins were in the interphase and phenolic phases. The aqueous phase was transferred to a microfuge tube and 500 μl (1 volume) isopropanol was added. The samples were stored at −70° C. for at least 60 minutes and then spun at 4° C. for 15 minutes. RNA precipitated and formed a white-yellow pellet at the bottom of the tube. The supernatant was removed and the RNA pellet was washed twice with 70% ethanol in DEPC $H_2O$. DEPC $H_2O$ is 0.1% Diethylpyrocarbonate in water, shaken well, incubated 2 hours 37° C., and autoclaved.

The RNA pellet was vacuum dried briefly for 10–15 minutes and then dissolved by vortexing in 50 μl DEPC $H_2O$ containing 0.5 μl RNase inhibitor (Boehringer Mannheim, 50 units/ml). The RNA was stored at −20° C. or −70° C.

4. Reverse Transcription (RT) Reaction

A RT master mix was prepared:

| RT Master Mix | Volume (μl) | Final Concentration |
|---|---|---|
| 25 mM $MgCl_2$ | 4 μl | 5 mM |
| 10X PCR buffer (PEC) | 2 | 1X |
| DEPC $H_2O$ | 1 | — |
| dGTP | 2 | 1 mM |
| dATP | 2 | 1 mM |
| dTTP | 2 | 1 mM |
| dCTP | 2 | 1 mM |
| RNase inhibitor (20 units/ml) | 1 | 1 u/μl |
| MULV reverse transcriptase | 1 | 2.5 u/μl |

-continued

| RT Master Mix | Volume (µl) | Final Concentration |
|---|---|---|
| Random hexamers | 1 | 2.5 u/µl |
| | 18 µl/sample | |

18 µl RT master mix was added to a thermalcycling tube. 2 µl RNA from the sample described above was added. 2 µl quantitation standard RNA with 10, 50, 100, 1000, 5000, 10,000 copies respectively, were added and kept at room temperature for 10 minutes. The samples were incubated 42° C. for 60 minutes, then 99° C. for 5 minutes, then held at 5° C.

5. PCR Amplification

A PCR master mix was prepared:

| PCR master mix | Volume (µl) | Final Concentrations |
|---|---|---|
| 25 mM MgCl$_2$ | 2 µl | 2 mM |
| 10X PCR buffer | 4 | 1X |
| sterile distilled H$_2$O | 31.5 | |
| | 37.5 µl/sample | |
| PCR sample tubes were prepared: | | |
| PCR master mix | 37.5 µl | — |
| Upstream primer PF526 | 1 | 0.5 nM |
| Downstream primer PR6780biotin | 1 | 0.5 nM |
| cDNA | 10 | — |
| Ampli Taq DNA polymerase | 0.5 | 2.5 units/50 µl |
| | 50 µl | |

The samples were overlayed with 40 µl mineral oil. The tubes were placed in a 70° C. prewarmed thermal cycler within 2 minutes of adding Ampli Taq to reduce nonspecific binding of primers and production of nonspecific products. Hot start is optional (see Ampli Taq directions).

Sequence of primer PF 526: ATT TCT GGA GAT GTC CCG TAG GAG AAC (SEQ ID NO:19).

Sequence of primer PR 678: Biotin-CAC ATC CTT GAG TGA TTA AGT TTG ATG A (SEQ ID NO:20).

The thermalcycling program was as follows:
1. 95° C., 2 minutes (1 cycle)
2. 95° C., 1 minute; 55° C., 45 seconds; 72° C., 45 seconds, (2 cycles)
3. 94° C., 1 minute; 60° C., 45 seconds; 72° C., 45 seconds, (28 cycles)
4. 72° C., 7 minutes (final extension)

6. Denature PCR Product

To denature the DNA, the samples were incubated at 95° C. for 5 minutes and then kept on ice.

7. EHA

300 µl/well blocking solution was added to Reacti-Bind Strepavidin Coated Polystyrene Strep Plates (Pierce Catalog #15120) and incubated overnight at 4° C. The blocking solution was removed by aspiration.

Blocking solution:
5×Denhardt's solution
1% gelatin (EIA grade, BIORAD)
250 µg/ml herring sperm DNA (Promega)

70 µl/well of premixed solution was added for solution hybridization. 5 µl denatured PCR product was mixed with 65 µl hybridization buffer and incubated 42° C., 1 hour.

Hybridization buffer:
5×saline sodium phosphate EDTA
5×Denhardt's solution
1 pmol HRP-labeled HPIV-1 HN specific probe The sequence of HRP-labeled HPIV-1 HN specific probe was HRP-TAC, CTT, CAT, TAT, CAA, TTG, GTG, ATG, CAA, TAT, ATG (SEQ ID NO:21). The sample was washed 20 times with 1×PBS 0.05% Tween-20. 200 µl/well TMB-EHA substrate (Life Technologies Catalog #15980-014) was added, and the sample was incubated 15 minutes 20° C. in the dark. The reaction was stopped by adding 50 µl/well 1N H$_2$SO$_4$. The O.D. of the sample was measured at 450 nm.

8. Interpretation of results

Samples with O.D.'s greater than or equal to the mean of the negative control plus 3σ of the negative control are considered positive. If the O.D. is less than this, it is considered negative.

To quantitate the copy number of HPIV-1 RNA in the original sample, the EHA O.D. of the standard curve was compared and the copy number with each sample was read. Table 6, below, discloses data obtained in the Example described above. Nasal samples were independently cultured and identified. Both positive and negative samples were analyzed according to the present invention.

TABLE 6

| | RT-PCR-EHA | | | |
|---|---|---|---|---|
| Specimen Group | No. Specimens | No. Positive | No. Negative | Mean of HPIV copy/mL |
| virus culture positive | 9 | 9 | 0 | 239607 |
| virus culture negative | 40 | 4 | 36 | 36528 |

The 4 positive samples from the virus culture negative samples were found to have a mean HPIV copy/ml of 36528 transcripts. The other negative samples had no copies of HPIV transcripts.

We claim:

1. A method for evaluating a biological sample for the presence or absence of human parainfluenza virus 1 infection, comprising the steps of
   (a) isolating RNA from a biological sample,
   (b) creating cDNA from the isolated RNA,
   (c) exposing the cDNA to a pair of oligonucleotide primers selected from SEQ ID NOs:1–9 or inverse complements of SEQ ID NOs:1–9 under conditions in which the primers will selectively amplify a human parainfluenza virus 1 sequence if the human parainfluenza virus 1 is present and will not amplify other sequences, wherein an amplification product is produced if the human parainfluenza virus 1 is present; and
   (d) determining whether the amplified product is present.

2. A method for evaluating a biological sample for the presence or absence of human parainfluenza virus 1 infection comprising the steps of
   (a) isolating RNA from a biological sample,
   (b) exposing the RNA to a labelled probe selected from SEQ ID NOs:1–9 under conditions wherein a hybridization reaction between the probe and a human parainfluenza virus sequence can occur, wherein hybridization between the probe and other species does not occur, and
   (c) examining the reaction to determine whether a hybridization product exists.

3. The method of claim 1 additionally comprising the step of exposing the cDNA to primer pairs specific for human parainfluenza virus 2, wherein the primer pairs comprise SEQ ID NOs:22 and 23, and human parainfluenza virus 3, wherein the primer pairs comprise SEQ ID NOs:25 and 26.

4. The method of claim 1 wherein the biological sample is a respiratory secretion.

5. The method of claim 1 wherein step (d) comprises attaching the product of step (c) to a marker enzyme and examining the products of step (c) for the marker.

6. The method of claim 5 wherein the marker enzyme is horseradish peroxidase.

7. The method of claim 2 wherein the primers or probes are SEQ ID NOs:19 and 20.

8. The method of claim 1 additionally comprising the step of attaching the amplification product to a solid support.

9. The method of claim 8 wherein the solid support is a microtiter dish.

10. The method of claim 1 wherein the amplification product is detected by hybridization of an oligonucleotide probe specific for a hemagglutinin neuraminidase ("HN-specific probe") sequence.

11. The method of claim 10 wherein the oligonucleotide probe is labelled with an enzyme.

12. A kit for the detection of human parainfluenza virus 1 comprising a pair of primers selected from SEQ ID NOs:1–9.

13. The kit of claim 12 further comprising a pair of primers specific for human parainfluenza virus 2 and a pair of primers specific for human parainfluenza virus 3, wherein the primer pairs comprise SEQ ID NOs:22, 23, 25 and 26.

14. The kit of claim 12 additionally comprising a HN-specific oligonucleotide probe.

15. The kit of claim 14 additionally comprising a pair of primers specific for human parainfluenza virus 2 and a pair of primers specific for human parainfluenza virus 3, wherein the primer pairs comprise SEQ ID NOs:22, 23, 25 and 26.

16. The kit of claim 14 wherein the HN-specific oligonucleotide probe is labelled.

17. The kit of claim 14 wherein the HN-specific oligonucleotide probe is linked to a protein suitable for attaching the probe to a solid support.

18. The kit of claim 15 wherein the HN-specific oligonucleotide probe is labelled.

19. The kit of claim 15 wherein the HN-specific oligonucleotides probe is linked to a protein suitable for attaching the probe to a solid support.

* * * * *